United States Patent [19]

Anderson

[11] 4,411,895

[45] Oct. 25, 1983

[54] METHOD FOR CONTROLLING BLUETONGUE DISEASE IN SHEEP

[76] Inventor: William G. Anderson, Rte. 1, Box 350, Ontario, Oreg. 97914

[21] Appl. No.: 363,828

[22] Filed: Mar. 31, 1982

[51] Int. Cl.$^3$ .............................................. A61K 31/66

[52] U.S. Cl. .................................................... 424/211

[58] Field of Search ......................................... 424/211

[56] References Cited

U.S. PATENT DOCUMENTS 3,179,560 4/1965 Hewitt et al. ....................... 424/211

OTHER PUBLICATIONS

Cole et al.—Chem. Abst, vol. 67 (1967), p. 63264t.

Wagner et al.-Chem. Abst., vol. 62 (1965), p. 16901d.

*Primary Examiner*—Sam Rosen

*Attorney, Agent, or Firm*—Paul F. Horton

[57] ABSTRACT

A method for the control of bluetongue disease amongst sheep by the application of O, O-dimethyl O-p-(dimethylsulfamoyl) phenyl phosphorothioate directly to the back of the animal. Such application of a chemotherapeutic dosage prevents contamination of the animal by the bluetongue virus carrying gnat (Culicoides).

3 Claims, No Drawings

METHOD FOR CONTROLLING BLUETONGUE DISEASE IN SHEEP

BACKGROUND OF THE INVENTION

1. Field of the Invention

This invention provides a new use for an old product, namely a novel way to prevent the transmission of bluetongue virus from the Culicoides gnat to sheep by treating the skin of the sheep and, more particularly the skin upon the back of the sheep to a chemotherapeutic dosage of sulfamoyl phenyl esters of organic phosphates.

2. Description of the Prior Art

The raising of sheep for both wool and food is an important industry in the United States, as well as in many other countries. This industry is currently being threatened by a viral disease known as bluetongue. Bluetongue was first reported in United States in 1952 but already is felt responsible for the decimation of the Big Horn sheep population of West Texas in 1967. While the effects of bluetongue are largely felt in the domesticated sheep industry, the disease can attack any ruminant with mortality being documented following disease outbreaks in mule deer, antelope, Big Horn sheep, as well as cattle. Death losses from bluetongue is usually in the 10-30% range. Abortion, early embryonic death, and malformed lambs are also a result of the disease. Another great economic loss caused by the disease is the loss of weight of feeder lambs and young sale rams which contract the disease. Another common occurrence due to the disease is the sterilization of rams for a period of up to six months following recovery from the disease even though the disease may have been mild. Sterilization may be permanent in more severe cases. Obviously, this problem can lead to late lambs or no lambs in small flocks.

The bluetongue virus is carried from one animal to another by a small gnat called Culicoides. When the gnat bites an infected animal it acquires the virus and carries it to the next animal it feeds on. Presently, there are two approaches to controlling the gnat to prevent disease. The first is to reduce the breeding sites of the gnat and the second is use of chemical pesticides. Presently there are no pesticides registered for gnat control and therefore reducing the breeding areas is the most important method. Draining stagnant pools of water significantly reduces or eliminates the breeding site of the gnats. Spraying breeding sites to control gnats is proven not economically feasible. It has been shown that even if all gnats are killed in one area, by the next day new ones move in from surrounding areas. Heretofore, there has not been an effective method for controlling transmission of the bluetongue disease.

Sulfamoylphenyl esters of organic phosphates have been used for controlling parasites attacking warm blooded animals as disclosed and claimed in U.S. Pat. No. 3,179,560 issued to R. I. Hewitt. Such esters have been found to be very effective systemic insecticides for destroying the parasites. As shown in the same patent, the compound has been found effective against gastrointestinal nematodes in sheep. In the treatment of nematodes, the compound was given orally.

SUMMARY OF THE INVENTION

The present invention comprises a method for controlling bluetongue disease in ruminants and more particularly for preventing the transmission of bluetongue virus to sheep from the Culicoides gnat by administering a chemotherapeutic dosage of sulfamoylphenyl esters of organic phosphates directly to the skin of the animal.

DETAILED DESCRIPTION OF THE INVENTION

The spread of bluetongue virus is by the bite of an insect, the Culicoides gnat, and for this reason the disease is seen only in certain areas and during certain times. The first cases of the season are sporadic and are usually seen in July when the weather gets hot. During August and September the spread of the disease is significant and whole flocks of sheep may be affected. In sheep, the virus of bluetongue multiplies in the cells which line the blood vessels and damage to the these cells occurs. Fluid escapes from the damaged blood vessels producing edema, swelling, and hemorrhage. These effects can be especially seen in the muzzle, lips and ears of the sheep but also occur in the heart, lung, liver, spleen, kidney and muscle. Mucous membranes may become so dark in color that they appear blue, thus giving the disease the name bluetongue.

The Culicoides gnats, the transmitters of the disease, breed between early summer and fall in areas of shallow water. The larva develop in the soft mud near the water's edge and feed on the organic matter in the water. In the spring, the larvae complete development and transform into the pupil stage and within a few days thereafter, the mature adult gnat will emerge and begin seeking a host for a blood meal. The gnats acquire the virus from infected animals and transmit it to the next animal they bite. Each generation of gnats requires about two weeks from egg to adult. There are many generations in one season.

Because of the very large number of gnats which are potential carriers of the bluetongue virus, and because the virus is transmitted to a host by the bite of the gnat, it would seem that a systemic insecticide such as sulfamoylphenyl esters of organic phosphates would be ineffective in preventing transmission of the disease. This, because the bite of the gnat itself transmits the disease, even though the gnat may be destroyed because of its contact with the insecticide. It has been found, however, that the systemic insecticide must also work as a repellent to prevent the gnat from biting, thus preventing the transmission of the virus to the host. The sulfamoyalphenyl organic phosphate of the present invention are represented by the general formula:

$$R_1O\underset{R_2O}{\overset{A}{\diagdown}}P-O-\!\!\!\left\langle\!\!\!\begin{array}{c}\phantom{x}\end{array}\!\!\!\right\rangle\!\!\!-SO_2N\underset{R_4}{\overset{R_3}{\diagup}}$$

wherein $R_1$ and $R_2$ are lower alkyl radicals of from one to four carbon atoms, A is a member of the group consisting of oxygen and sulfur atoms, and $R_3$, $R_4$ are members of the group consisting of hydrogen and lower alkyl radicals. The following examples will serve to show administration and results of a 13.2% solution of O,O-dimethyl O-p(dimethylsulfamoyl) phenyl phosphorothioate, sold under the trademark WARBEX.

EXAMPLE 1

During the summer of 1980, on a flock of 200 sheep, WARBEX was administered to one ram by saturating the skin of the ram at a rate of 0.16 cc per pound of weight of the ram. The solution was delivered onto the back of the ram by syringe at five different locations beginning with the head and ending at the tail of the ram. The ram was the only animal of the flock which did not develop bluetongue. This result led to the conclusion that the WARBEX thus administered prevented the ram from being bitten by the Culicoides gnats.

EXAMPLE 2

During the year 1981, also on a flock of 200 sheep, all the sheep were given one treatment of WARBEX at the rate of 0.16 cc per pound for all mature sheep and at the rate of 0.15 cc per pound for lambs. Of the flock of 200, only four cases of bluetongue were detected. All four cases were mild and were in lambs only. The conclusion drawn from this experiment was that more than one treatment per season should be administered. It is recommended that a treatment be given every 35–40 days.

EXAMPLE 3

In the year 1981 a second flock of sheep of 100 head was treated with WARBEX in the same manner as previously indicated. One ram was purchased and added to the flock, untreated. The ram was the only one of the flock which developed bluetongue disease.

These examples indicate the effectiveness of treatment of sheep to their skins by a solution of WARBEX. It must be concluded that the WARBEX either acts as a repellent, preventing the gnat from biting the sheep or, in the alternative, the WARBEX is effective to destroy the virus once implanted by the bite of the Culicoides gnat.

While specific dosages have been given in examples and are recommended, it is obvious that changes of dosage and timing of dosage may be changed without detracting from the inventive concept herein. It is also obvious that different dosages and timing of dosages may be used for ruminants of various types.

I claim:

1. A method for preventing the transmission of bluetongue virus to sheep from the Culicoides gnat which comprises administering to the animal a chemotherapeutic dosage of a compound of the formula:

$$\begin{array}{c} R_1O \\ \diagdown \\ R_2O \end{array} \overset{A}{\underset{\|}{P}} - O - \underset{}{\bigcirc} - SO_2N \begin{array}{c} R_3 \\ \diagup \\ \diagdown \\ R_4 \end{array}$$

wherein $R_1$ and $R_2$ are lower alkyl of from 1 to 4 carbon atoms, A is a member of the group consisting of oxygen and sulfur atoms, and $R_3$ and $R_4$ are members of the group consisting of hydrogen and lower alkyl, which dosage is administered directly to the skin of the animal.

2. A method according to claim 1 wherein said dosage is administered onto the back of the animal from head to tail.

3. A method according to claim 1 wherein the compound is O,O-dimethyl O-p-(dimethysulfamoyl) phenyl phosphorothioate.

* * * * *